United States Patent [19]
Gent et al.

[11] Patent Number: 5,221,500
[45] Date of Patent: Jun. 22, 1993

[54] MECHANICAL IN SITU CUROMETER

[75] Inventors: Alan N. Gent, Cuyahoga Falls; George S. Fielding-Russell; Ahmet Talug, both of Stow, all of Ohio

[73] Assignee: The Goodyear Tire & Rubber Company, Akron, Ohio

[21] Appl. No.: 911,816

[22] Filed: Jul. 10, 1992

[51] Int. Cl.$^5$ .............................. B29C 35/00
[52] U.S. Cl. .................... 264/40.1; 264/40.6; 73/841; 73/843; 425/29; 425/155; 425/169
[58] Field of Search ............ 264/40.1, 40.6, 319; 425/29, 150, 155, 162, 169; 73/841, 843

[56] References Cited

U.S. PATENT DOCUMENTS

| | | | |
|---|---|---|---|
| 3,494,172 | 2/1970 | Juve et al. | 73/843 |
| 3,686,933 | 8/1972 | Sokolov et al. | 73/843 |
| 3,718,721 | 2/1973 | Gould et al. | 425/29 |
| 3,769,830 | 11/1973 | Porter et al. | 73/843 |
| 3,819,915 | 6/1974 | Smith | 264/40.1 |
| 5,158,720 | 10/1992 | Levy | 264/40.1 |

*Primary Examiner*—Jill L. Heitbrink
*Attorney, Agent, or Firm*—David E. Wheeler

[57] ABSTRACT

An in situ curometer has been developed to follow the cure of thick articles during molding, by measuring continuously the dynamic mechanical properties (shear modulus and loss angle). The apparatus is designed to provide cure data on curable articles such as rubber products and components in situ, during the curing of the article, to improve manufacturing cure efficiencies. The curometer is a small-scale version of an Oscillating Disk Rheometer, designed to operate through a mold wall. An approximate theoretical treatment has been developed to relate the observed torque and loss angle to the dynamic properties of the rubber compound.

5 Claims, 5 Drawing Sheets

MECHANICAL IN SITU CUROMETER

BACKGROUND

Many methods have been proposed for studying the cure kinetics of rubber compounds. Mechanical properties of rubber specimens are generally measured as a function of cure time. Decker, et al, Rubber Chem. Technol. 36, 451 (1963), developed an oscillating disk rheometer which, in various forms, has been widely adopted to measure the dynamic mechanical properties of a single specimen continuously during vulcanization. A profiled steel disk is embedded within a disk of the compound under study, and subjected to forced torsional oscillations. Values of torque and phase angle between torque and angular displacement are measured as a function of time of cure. The amplitude of oscillation is small, typically 1-3 degrees, and the frequency is typically 1.7 Hz.

Commercial rheometers are currently used for testing the cure properties of rubber compounds in laboratory samples. There are about twenty companies worldwide producing commercial rheometers. The largest producers of such apparatus are Monsanto Chemical Co., Instruments Group, Toyo Selki Selsolsu-Sho, Ltd., and Zwick of America, Inc. The commercial rheometer is a large, complex, stand alone off-line, lab only device wherein the sample holding portion of the machine is as important to the results obtained as the sensing arm which measures the torque of the oscillating disk. Consequently, the current commercial rheometer is also expensive. There is currently no known device for measuring in situ the cure status of a fully formed elastomeric product during manufacture.

It is an object of the present invention to provide a method and apparatus whereby the cure properties of a fully formed elastomeric article can be measured in situ in a mold to increase manufacturing efficiencies. It is also an object of the present invention to provide such apparatus on a much smaller scale and at 1/10 to 1/20 the cost of a commercial rheometer. Other objects of the invention will be apparent from the following description and claims.

SUMMARY OF THE INVENTION

The invention relates to a method and apparatus for the in situ monitoring of the cure status of a completed elastomeric article. The method comprises the steps of (a) providing a means for inserting monitoring equipment into a mold without affecting the pressure and temperature within the mold, (b) inserting monitoring equipment into the mold, (c) initiating cure of the article in the mold, (d) monitoring the properties of the article at preselected time intervals during cure, (e) continuing the cure to the point where physical properties of the article monitored by the monitoring equipment match preselected parameters, and (f) discontinuing the cure.

The apparatus of the invention is a miniaturized version of the oscillating disk portion of a commercial rheometer, and does not have a sample holding portion. The apparatus comprises (a) a profiled steel disk adapted for contacting an elastomeric product in a mold during curing, (b) a drive shaft connected to the disk which provides a sealing relationship between the mold and the drive shaft, (c) a means for causing oscillation of the drive shaft and the disk, (d) means for measuring the torque on the drive shaft during oscillation, (e) a means for sensing shaft angular displacement, and (f) a means for connecting the apparatus to a mold.

DETAILED DESCRIPTION OF THE INVENTION

Figure 1:
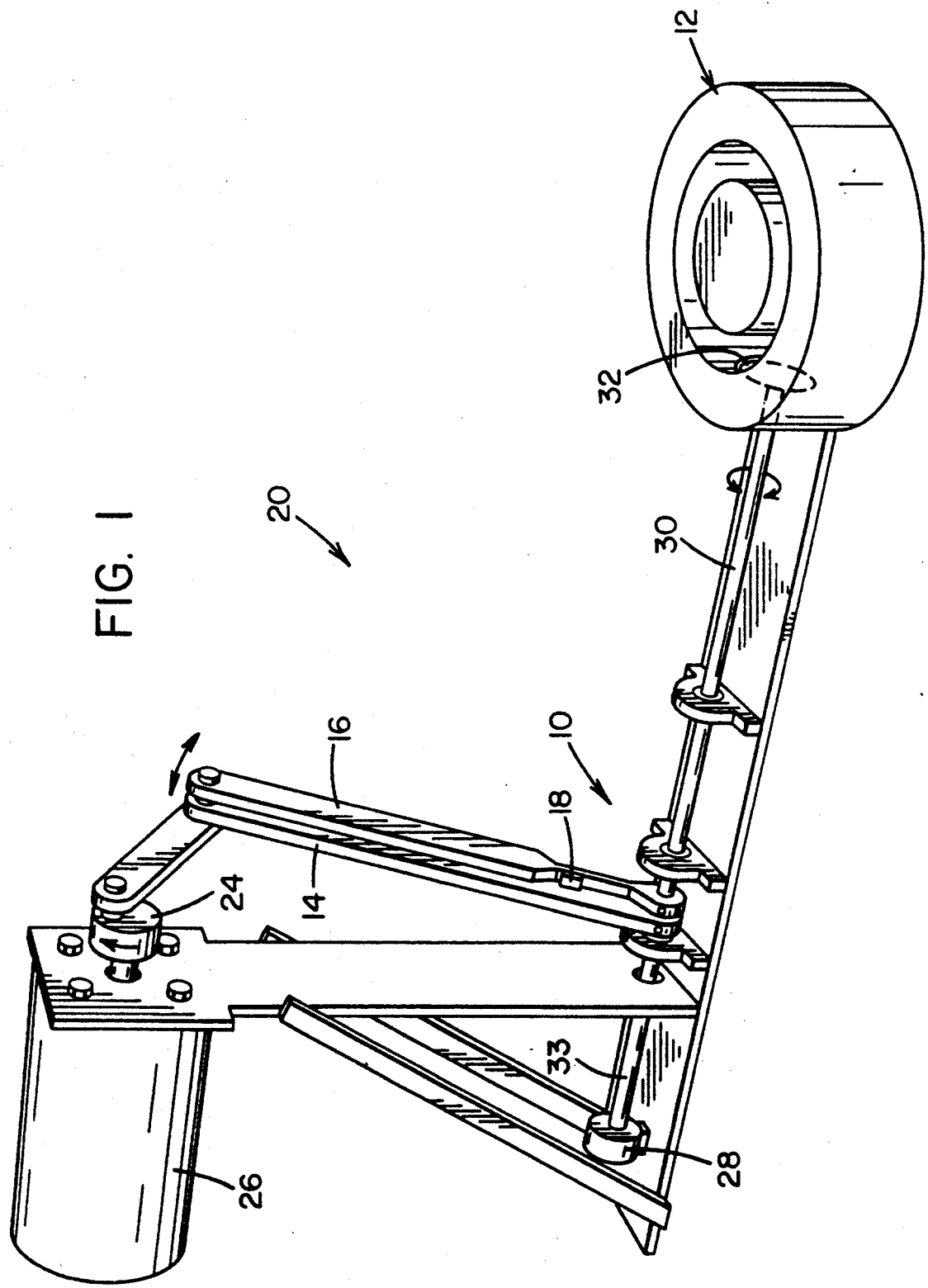
FIG. 1 illustrates the apparatus of the curometer portion of the apparatus of the invention.
Figure 2:
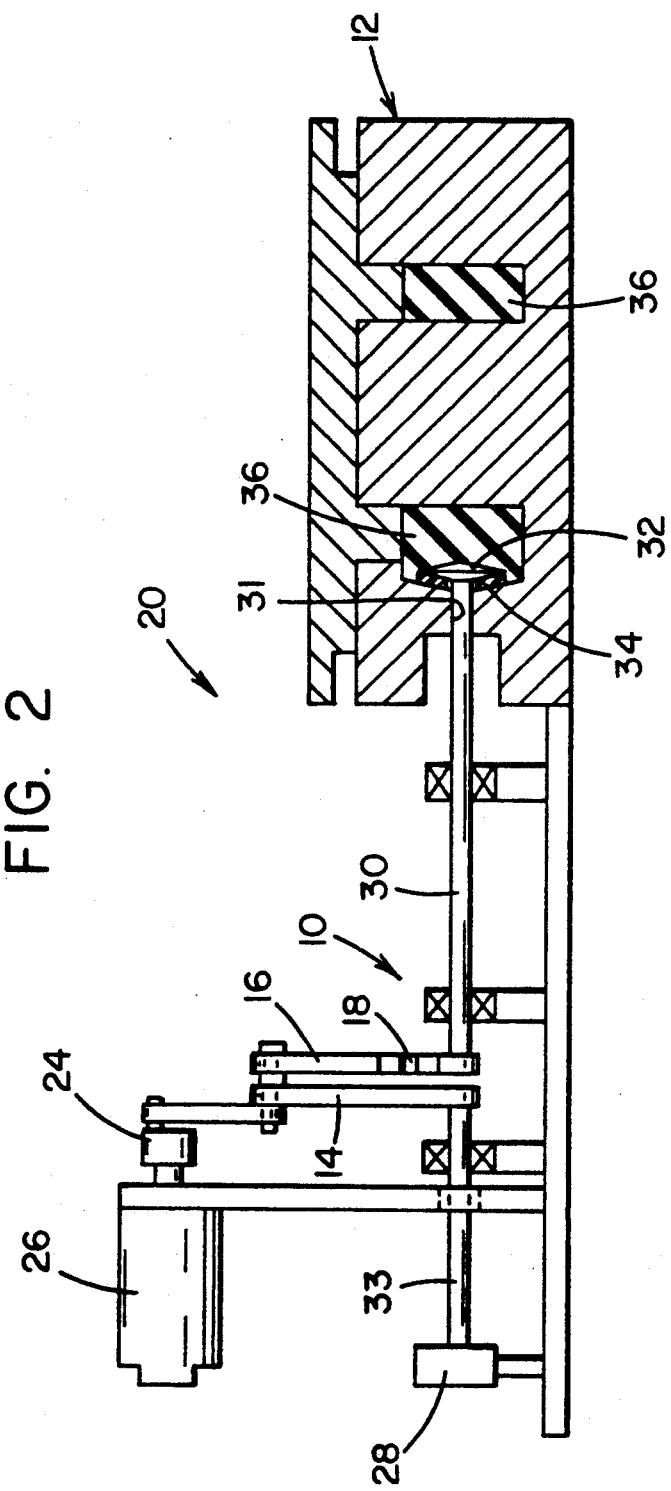
FIG. 2 illustrates a curometer attached to a curing mold.
Figure 3:
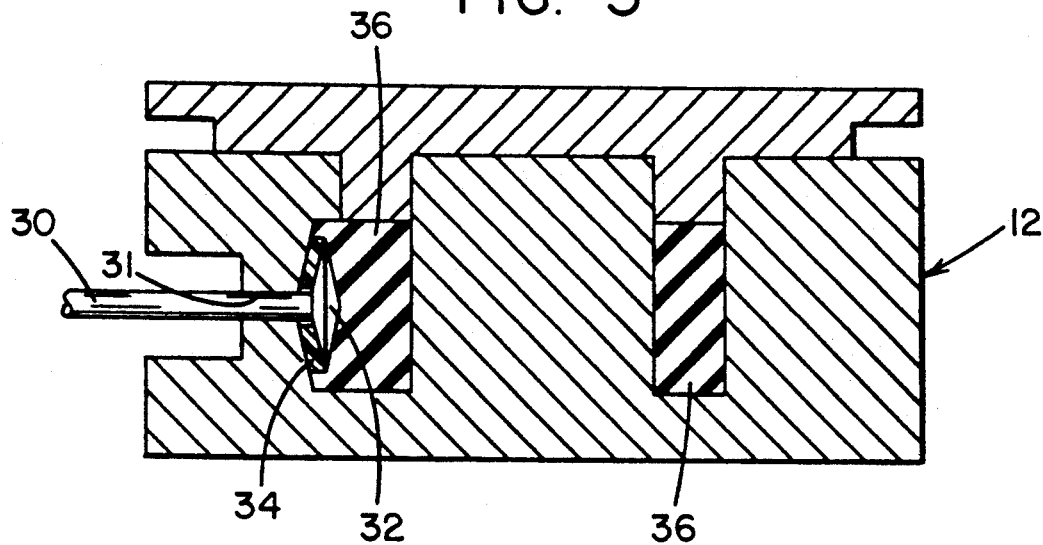
FIG. 3 illustrates a disk of the curometer in the mold cavity.

With reference now to FIGS. 1-3, the apparatus 20 of the invention comprises an oscillating disk torque measuring device 10 in conjunction with a mold 12. The oscillating disk torque measuring device 10 comprises a profiled disk 32 for contacting rubber in the mold, a motor 26 for driving the disk through eccentric 24 which provides the oscillatory motion of disk 32, torque arm 16 which transfers torque from the eccentric to drive shaft 30, said drive shaft being connected to disk 32. Strain gauges 18 measure the amount of torque transferred to the drive shaft. Displacement arm 14 is used in the illustrated apparatus to measure the angular displacement of torque arm 16, and said displacement can be transferred to potentiometer 28 to provide a visual display of the range of motion of the disk.

The elastomeric product 36 cured in the mold 12, a tire for example, is flowable at high temperatures, before the curing takes place, and elastomer from the product 36 tends to flow around disk 32. Accordingly, drive shaft 30 is provided with a silicon rubber "0" ring or washer 34 which provides a seal between the disk 32 and the hole 31 in the mold 12.

Hole 31 is drilled in the mold 12 to provide access for disk 32, and since the oscillating disk distorts the rubber of the product, it is preferred to drill the hole 31 in the mold at a location where the deformation is not critical to the rubber product, or at a position where the distorted rubber can be buffed. If the product can tolerate a molded protuberance about 25 mm in diameter and about 4 mm in height, no buffing will be required.

Those skilled in the art will recognize that for most molded and cured articles, especially large articles, there is not a completely uniform temperature distribution in a mold. It is generally accepted in the art that although curing rates may be different in different parts of the mold, that monitoring a particular point in the mold will give a fair indication of the overall cure status of the article if the relative cure rates in different parts of the article are known or can be determined.

In the assembly of the apparatus, disk 32 is placed inside the mold 12 and drive shaft 30 is placed in hole 31 and attached to disk 32.

Since, in effect, the mold 12 stands in the relationship of the sample holder in conventional rheometers, it is important that the measuring device 10 be rigidly and firmly attached to the mold. The measuring device 10 can be bolted directly to the mold or be attached through a rigid framework structure.

The curemeter operates by measuring the dynamic mechanical properties of the rubber compound as vulcanization proceeds. The shaft 30 and disk 32 are oscillated through a small angle at intervals during vulcanization of the rubber compound 36. From the torque required to oscillate the disk, the dynamic shear modulus of the rubber can be calculated. Loss angles can also be determined from simultaneous measurements of torque and angular displacement as a function of time.

The mold with an inserted disk probe is shown schematically in FIG. 3. Flow of the rubber compound around and behind the oscillating disk and along the shaft through the mold wall to the exterior was prevented by a seal comprising silicon rubber washer 34.

The disk 32 is adapted to contact a surface only of the molded article 36 during curing. This arrangement minimizes the distortion of the elastomeric product. Those skilled in the art will recognize that this sample contact differs from the sample treatment in commercial rheometers where the disk is embedded in the sample using the MDR (Moving Die Rheometer), or ODR (Oscillating Disk Rheometer) techniques.

As shown in FIGS. 1 and 2, the shaft 30 and disk 32 are made to oscillate by a motorized cam. Measurements of instantaneous torque are obtained from strain-gage transducers 18 applied to the drive linkage. Simultaneous measurements of the amount of torsional displacement of the disk are obtained from a potentiometer 28 connected to a separate shaft 33 that oscillates at the same frequency and amplitude as the drive shaft 30. The sinusoidal outputs from the transducers are collected by a data acquisition system with a sampling rate of 20 Hz, and fitted to sinusoidal relations by a curve-fitting software routine, as described below.

In the illustrated embodiment, the disk was subjected to torsional oscillations of amplitude ±2.7°, at a relatively low frequency of 25 cycles per minute.

The torque measuring system was calibrated by deadweight loading. The potentiometer employed for measuring torsional oscillation was calibrated by direct measurement of the angular displacement of the rotor shaft at a position near the mold wall. The amplitude decreased slightly, from ±2.7° to ±2.6°, as the applied torque increased from 0 to 0.1 N-m.

The total torque required to oscillate the rigid disk 32 is given by the torsional displacement of the disk and the torsional stiffnesses of both the rubber article being cured $S_1$ and the rubber disk seal $S_2$. The torque on a rigid circular disk adhering to a semi-infinite elastic half-space is given by M. Olesiak ("Some Punch and Crack Problems in the Theory of Elasticity," in "Applications of Integral Transforms in the Theory of Elasticity", ed. by I. N. Sneddon, Springer Verlag, N.Y., 1975, pp. 99-169).:

$$M_1 = \frac{16}{3} G_1 \theta a^3$$

where $G_1$ is the shear modulus of the rubber, $\theta$ is the rotation angle, and "a" is the radius of the disk. Treating the rubber seal as a solid disk subjected to torsion through the same angle $\theta$, the corresponding torque $M_2$ is given by $$M_2 = \frac{\pi}{2} G_2 \theta \frac{a^4}{L}$$

where $G_2$ is the shear modulus of the seal, "a" is the external radius and L is its thickness. Thus, the total torque on the disk is $$M_{total} = \left[ \frac{16}{3} G_1 a^3 + \frac{\pi}{2} G_2 \frac{a^4}{L} \right] \theta$$

When $M_1 = M_2$ and $G_1 = G_2$, then $L \approx a/3$. Therefore, in order to make the contribution $M_1$ to the total torque from the rubber compound larger than that $M_2$ from the rubber disk seal, we require $L \geq a/3$, and $G_2$ (seal) $< G_1$ (compound studied). The dimensions chosen were L=3 mm, a=6.4 mm.

The apparatus of the invention can be used with, for example, production press molds or injection molds, in the manufacture of elastomeric products. The apparatus can also be used as an inexpensive laboratory device to measure the cure properties of rubber samples.

Experiments have been carried out with unfilled and carbon-black-filled compounds of natural rubber, using a mold that makes cylindrical rubber rings having a thickness of 25 mm, a 63 mm external diameter and a 36 mm internal diameter. Measurements with the curometer are described here and compared with those obtained with a Monsanto oscillating disk rheometer.

Cure times measured by the curometer were about the same as those obtained with the Oscillating Disk Rheometer. Modulus values inferred from the measured torques were compared with directly-measured values obtained from load deflection curves for fully-cured specimens.

The invention is further illustrated with reference to the following examples.

EXAMPLE 1

(a) Materials

The materials used in this study were unfilled and carbon-black-filled natural rubber compounds. Compound formulations in parts by weight were:

| INGREDIENT | UNFILLED | FILLED |
|---|---|---|
| Natural Rubber (SMR-L) | 100 | 100 |
| Carbon Black (N300) | 0 | 50 |
| Stearic Acid | 2.0 | 2.0 |
| Processing Oil (Sundex 790) | 0 | 5.0 |
| Phenyl-a-naphthylamine | 1.0 | 1.0 |
| Accelerator (MBTS) | 0.6 | 0.6 |
| Sulfur | 2.5 | 2.5 |

These compounds were vulcanized in the ring mold shown in FIG. 3, using an electrically-heated press. The mold was wrapped with fiberglass in order to reduce heat loss through its cylindrical surface. The mold pressure was about 2 MPa and the press temperature was set at 140° C. A probe thermocouple was inserted through the mold wall at a position near the center of the curing sample. It was found that the temperature at this location rose to the cure temperature (140°±1° C.) in about 20 minutes for the unfilled NR compound, and slightly faster, in about 15 minutes, for the filled compound, probably because of its greater thermal conductivity (D. Kong, et al, Rubber Chem. Technol. 60, 140 (1987)).

(b) Experimental Procedure

First, the mold was preheated in the press for about 30 minutes. A pre-shaped ring of the rubber compound was then placed into the mold which was closed and subjected to pressure. This took about 3 minutes. Measurements were carried out as follows: The rotor was started and data recorded for 10 seconds. The rotor was then switched off for 5 minutes. A second series of measurements was then carried out for 10 seconds, and so on, until the cure was complete.

Figure 4:
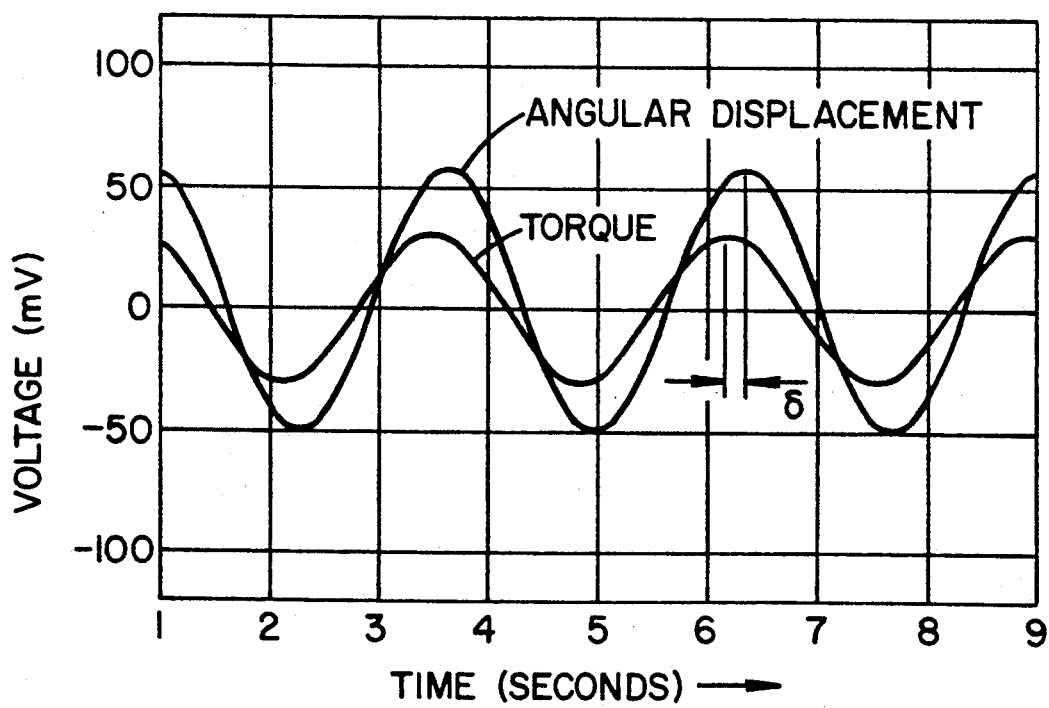
FIG. 4 illustrates graphically the phase angle determined by the curometer.

Values of torque M and torsional displacement $\theta$ were fitted to sinusoidal relations as a function of time using a curve-fitting program ("Sigma Plot-4.0"):

| TORQUE | $M = M_0\sin(wt + \delta_1) + d_1$ |
| DISPLACEMENT | $\theta = \theta_0\sin(wt + \delta_2) + d_2$ | where the quantities $M_0$, $\theta_0$, $\delta_1$, $\delta_2$, were obtained as best-fit values. $M_0$ represents the maximum torque. The phase angle $\delta$ is given by: $\delta = \delta_1 - \delta_2$, as shown in FIG. 4.

Figure 5:
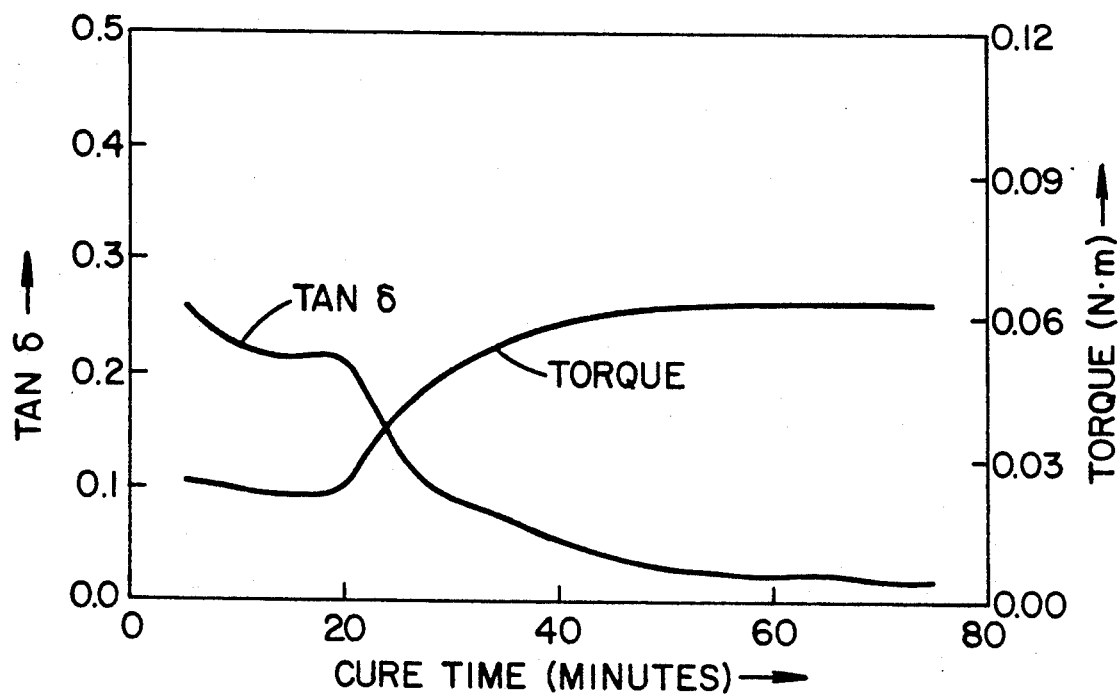
FIGS. 5 and 6 illustrate values of maximum torque and phase angle for unfilled and filled (respectively) natural rubber as functions of cure time.
Figure 6:
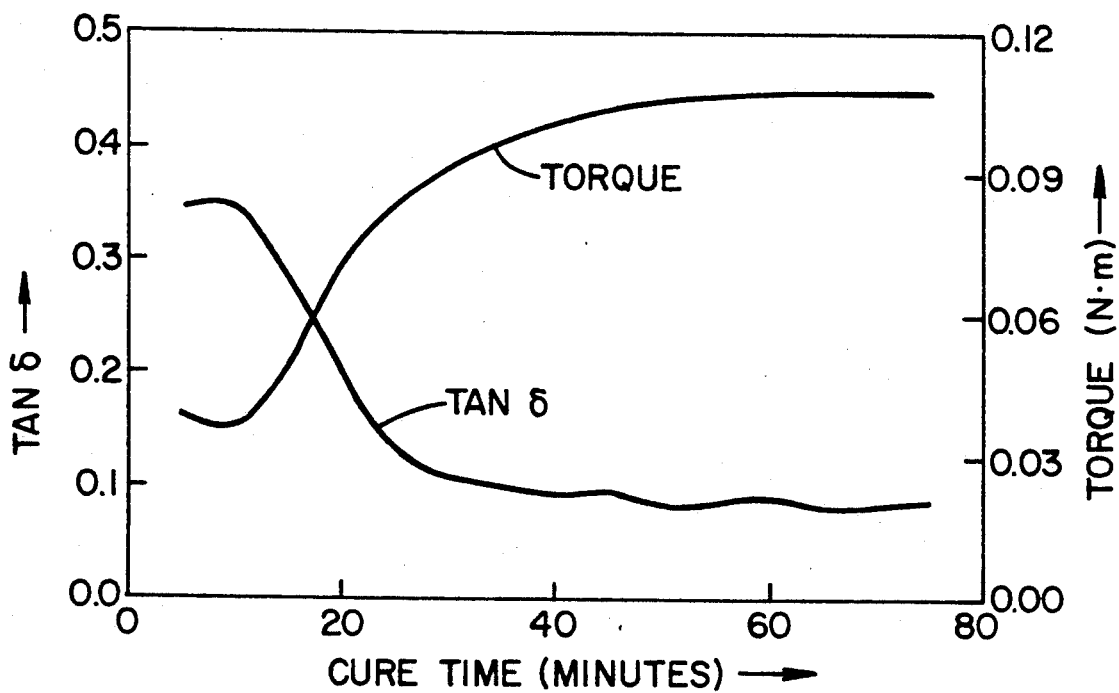
Figure 7:
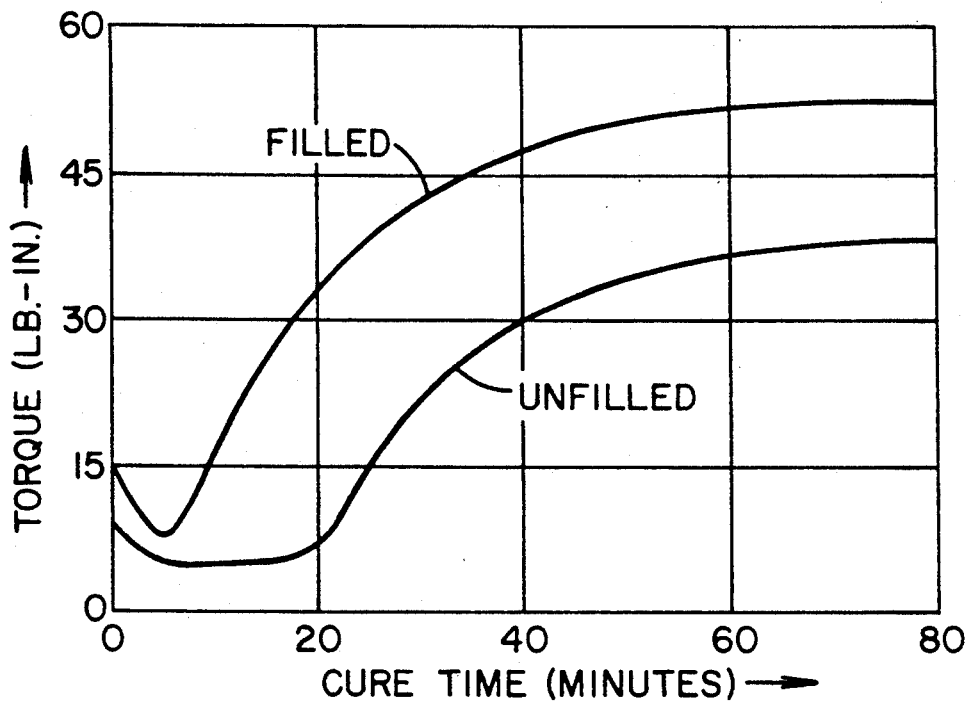
FIG. 7 illustrates cure curves of the same compounds (see FIGS. 5 and 6) obtained with a commercial oscillating disk rheometer for comparison with the apparatus of the invention.
Figure 8:
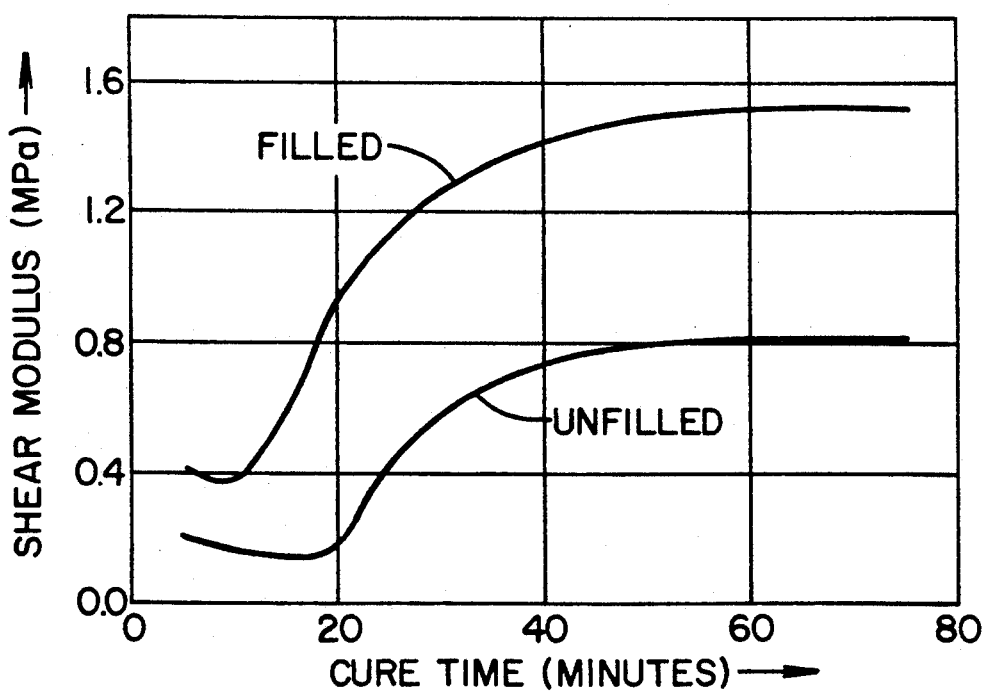
FIG. 8 illustrates variation of G with cure time as calculated from results obtained by a curometer of the invention.

Values of maximum torque and phase angle for unfilled and filled NR compounds are plotted in FIGS. 5–6 as functions of cure time. Note that the values plotted in FIGS. 5 and 6 have not been corrected for the contributions to torque and phase angle from the rubber disk seal. From the curves of maximum torque versus cure time, the time to reach 50% and 90% of the final torque were determined. They are given in Table 1. They were somewhat shorter for the filled compound, indicating a somewhat more rapid cure. Cure curves for the same compounds obtained with the Monsanto Oscillating Disk Rheometer are shown in FIG. 7. They are in good agreement with curometer results, as shown in FIG. 8.

Measured values of loss angle were found to be somewhat variable. The precision of these measurements might be improved by using a potentiometer with higher sensitivity and increasing the sampling rate of the data acquisition system.

Values of shear modulus G were calculated from the relation $$G = \frac{3}{16\theta a^3}(M_{total} - M_2)$$

where $M_2$ is the torque due to the seal. FIG. 8 shows the variation of G with cure time. Values of shear modulus were also calculated from the Monsanto Rheometer results using a relation applicable to an embedded biconical disk in a cylindrical cavity of the same height:

$$G = \frac{3M\alpha}{4\pi a^3 \theta}$$

where M is the torque at maximum strain, "a" is the radius of the disk, $\alpha$ is the cone angle, and $\theta$ is the oscillation amplitude.

Values of Young's modulus E for fully-cured samples were measured by subjecting the molded cylindrical rings to small compressions in an Instron test machine at 140° C. The shear modulus G was then taken to be E/3. Values of final shear modulus obtained in this way are compared in Table 2 with those deduced from curometer and Monsanto Rheometer measurements. Whereas the values deduced from curometer torque measurements are seen to be closed to those measured directly on fully-cured specimens, the values from the Monsanto Rheometer were much lower. The reason for this discrepancy is not known. It may be due to slippage in the Rheometer.

TABLE 1

Comparison of cure times at 140° C.

| | $t_{50}$ (min) | | $t_{90}$ (min) | |
| Compounds | Curometer | Monsanto Rheometer | Curometer | Monsanto Rheometer |
| --- | --- | --- | --- | --- |
| Unfilled NR | 27 | 30 | 42 | 51 |
| Filled NR | 20 | 18 | 38 | 41 |

TABLE 2

Comparison of values of final shear modulus (MPa) at 140° C.

| Compounds | Curometer | Compression Measurements | Monsanto Rheometer |
| --- | --- | --- | --- |
| Unfilled NR | 0.8 | 0.6 | 0.3 |
| Filled NR | 1.5 | 1.4 | 0.5 |

While specific embodiments of the invention have been illustrated and described, those skilled in the art will recognize that the invention may be variously modified and practiced without departing from the spirit of the invention. The scope of the invention is limited only by the following claims.

What is claimed is:

1. A method for monitoring in situ the cure of a fully formed elastomeric article in a mold comprising the steps of
   (a) providing a hole in the wall of the mold,
   (b) inserting a profiled steel disk into the mold such that said steel disk contacts the rubber article in the mold while being connected to a drive shaft located in the hole of step (a) in the wall of the mold, wherein the drive shaft is fitted with means to provide a seal between the drive shaft and the mold,
   (c) connecting said drive shaft to a means for rotating the drive shaft and profiled disk through a preselected degree of rotation,
   (d) providing means for measuring the torque needed to rotate said shaft and disk through said preselected degree of rotation, said profiled steel disk and said means for measuring torque comprising monitoring equipment,
   (e) initiating cure of the article in the mold,
   (f) monitoring the properties of the article at preselected time intervals during cure by taking torque measurements using said monitoring equipment,
   (g) continuing the cure to the point where physical properties of the article monitored by the monitoring equipment match preselected parameters, and
   (h) discontinuing the cure.

2. The method of claim 1 wherein the monitoring step further comprises measuring values of torque, and phase angle between torque and angular displacement, as a function of time and cure.

3. The method of claim 1 further comprising the step of buffing or finishing the elastomeric article at the point of contact between the article and the profiled disk.

4. The method of claim 1 further comprising the step of providing a feed back loop whereby the cure is automatically stopped when preset cure measurements are obtained.

5. An apparatus for in situ monitoring of the cure of a fully formed elastomeric article, said apparatus comprising
   (a) a profiled steel disk adapted for contacting an elastomeric product in a mold during curing,
   (b) a drive shaft connected to said disk and providing a sealing relationship between said mold and said drive shaft,
   (c) means causing oscillation of said drive shaft and said disk connected to said drive shaft,
   (d) means for measuring the torque on said drive shaft during oscillation,
   (e) means for sensing shaft angular displacement,
   (f) means for comparing measured data with a preset value, and
   (g) means for stopping the cure when said preset value is obtained.

* * * * *